United States Patent
Ebert et al.

(10) Patent No.: US 11,780,802 B2
(45) Date of Patent: Oct. 10, 2023

(54) ORGANIC SULFONIC ACID SALTS OF AMINO ACID ESTERS AND PROCESS FOR THEIR PREPARATION

(71) Applicant: BASF SE, Ludwigshafen am Rhein (DE)

(72) Inventors: Sophia Ebert, Ludwigshafen am Rhein (DE); Bjoern Ludolph, Ludwigshafen am Rhein (DE); Dawid Marczewski, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/770,080

(22) PCT Filed: Nov. 27, 2018

(86) PCT No.: PCT/EP2018/082663
§ 371 (c)(1),
(2) Date: Jun. 5, 2020

(87) PCT Pub. No.: WO2019/110371
PCT Pub. Date: Jun. 13, 2019

(65) Prior Publication Data
US 2021/0188764 A1    Jun. 24, 2021

(30) Foreign Application Priority Data

Dec. 5, 2017    (EP) .................................... 17205357

(51) Int. Cl.
| C07C 227/22 | (2006.01) |
| C07C 303/22 | (2006.01) |
| C07C 309/30 | (2006.01) |
| C07C 229/08 | (2006.01) |
| C07C 309/04 | (2006.01) |
| C07C 309/31 | (2006.01) |

(52) U.S. Cl.
CPC .......... C07C 227/22 (2013.01); C07C 303/22 (2013.01); C07C 309/30 (2013.01); C07C 229/08 (2013.01); C07C 309/04 (2013.01); C07C 309/31 (2013.01)

(58) Field of Classification Search
None
See application file for complete search history.

(56) References Cited

U.S. PATENT DOCUMENTS

| 3,211,781 A | * | 10/1965 | Hino ..................... C07C 227/22 |
| | | | 560/155 |
| 3,939,200 A | | 2/1976 | Emmons et al. |
| 3,954,845 A | | 5/1976 | Martinsson et al. |
| 4,154,956 A | | 5/1979 | Ueda et al. |
| 4,194,052 A | | 3/1980 | Lewis et al. |
| 4,550,137 A | * | 10/1985 | Dowbenko .......... C08K 5/0025 |
| | | | 525/162 |
| 2014/0039219 A1 | | 2/2014 | Tien et al. |
| 2016/0068471 A1 | | 3/2016 | Palou et al. |

FOREIGN PATENT DOCUMENTS

| FR | 2977585 B1 | 8/2015 |
| GB | 934965 A | 8/1963 |
| JP | 50-093921 A | 7/1975 |
| JP | 09-301937 A | 11/1997 |
| SU | 1276661 A1 | 12/1986 |
| WO | WO-2008083967 A2 | 7/2008 |
| WO | WO-2015172158 A1 | 11/2015 |
| WO | WO-2016150953 A1 | 9/2016 |

OTHER PUBLICATIONS

International Search Report for PCT/EP2018/082663 dated Jan. 4, 2019.
Written Opinion of the International Searching Authority for PCT/EP2018/082663 dated Jan. 4, 2019.
Camacho et al., "Efficient Microwave-Assisted Synthesis of Ionic Esterified Amino Acids", Molecules, vol. 16, No. 10, Oct. 19, 2011, pp. 8733-8744.
European Search Report for EP Patent Application No. 17205357.1, dated Jun. 13, 2018, 5 pages.
Grubb et al., "The synthesis and physical evaluation of 5-alkoxy-1,3-thiazoles prepared via Lawesson's reagent-mediated cyclisation of a-benzamido esters", Liquid Crystals, vol. 36, No. 5, May 2009, pp. 443-453.
International Preliminary Report on Patentability received for PCT Patent Application No. PCT/EP2018/082663, dated Jun. 18, 2020, 9 pages.
Penney et al., "A simple method for the synthesis of long-chain alkyl esters of amino acids", The Journal of Organic Chemistry, vol. 50, No. 9, May 1, 1985, pp. 1457-1459.

(Continued)

*Primary Examiner* — Amy C Bonaparte
(74) *Attorney, Agent, or Firm* — Faegre Drinker Biddle & Reath LLP

(57) ABSTRACT

The application relates to a process for the synthesis of organic sulfonic acid salts of amino acid esters comprising the steps of (i) reacting at least one lactam with at least 3 carbon atoms in the lactam ring with at least one organic sulfonic acid in an aqueous solution, (ii) esterification of the organic sulfonic amino acid salt of step (i) with at least one alcohol with at least 8 carbon atoms comprising at least one hydroxyl group, (iii) optionally removal of water and/or removal of excess alcohol of step (ii). The application also relates to organic sulfonic acid salts of amino acid esters of the general formula (I).

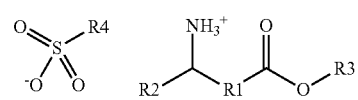

12 Claims, No Drawings

(56) References Cited

OTHER PUBLICATIONS

Tsushima et al., "Fluorine-containing amino acids and their derivatives. 5. Synthesis of novel fluorinated analogs of the antitumor agent, methotrexate", Heterocycles, vol. 23, No. 1, 1985, pp. 45-49.
Xue et al., "Exceptionally Strong Electronic Coupling in Crystalline Perylene Diimides via Tuning", Chemistry of Materials, vol. 23, No. 11, May 10, 2011, pp. 2689-2692.
Schwarz A, et al., "Poverkhnostno-aktivnye veshhestva. Ikh khimija i tekhnicheskie primenenija—Their chemistry and technical applications", Monography, 1953, pp. 387-391.

* cited by examiner

ORGANIC SULFONIC ACID SALTS OF AMINO ACID ESTERS AND PROCESS FOR THEIR PREPARATION

CROSS-REFERENCE TO RELATED APPLICATIONS

This application is a national stage application (under 35 U.S.C. § 371) of PCT/EP2018/082663, filed Nov. 27, 2018, which claims benefit of European Application No. 17205357.1, filed Dec. 5, 2017, both of which are incorporated herein by reference in their entirety.

The invention relates to a process for the synthesis of organic sulfonic acid salts of amino acid esters. The invention additionally relates to organic sulfonic acid salts of amino acid esters.

Organic sulfonic acid salts of esters from long-chain alcohols and amino acids are described in the literature. Methane sulfonic acid salts of amino acid esters are synthesized from amino acids and alcohols using methane sulfonic acid at elevated temperatures (C. L. Penney et al., J. Org. Chem. 1985, 50, 1457-1459; A. M. Grubb et al., Liquid Crystals 2009, 36, 443-453; R. Ceron-Camacho et al., Molecules 2011, 16, 8733-8744)

Amino acid esters from amino acids with equal or more than 3 carbon atoms can be synthesized from the corresponding lactams. This synthesis includes as a first step the ring-opening of the lactam to the amino acid in presence of an acid, and as a second step the esterification reaction with an alcohol.

FR2977585B1 discloses a process for the synthesis of α-amino acid esters of $C_7$- to $C_{36}$-alcohols from the amino acid or its salt in presence of an acidic catalyst in the presence of water, starting from amino acids or salts thereof.

US2014/0039219A1 discloses a method for making 6-aminocaproic acid as an active pharmaceutical ingredient by using a solubility regulating agent to decrease water solubility of the 6-aminocaproic acid. Organic solvent is disclosed for extraction of 6-aminocaproic acid intermediates from the reaction mixture.

U.S. Pat. No. 3,939,200 discloses novel acyl-containing amine hydrochlorides that are produced by converting amino groups to an acid salt by reaction with hydrochloric acid and reacting the resulting product with an alkanolamine or diol in an inert liquid medium while passing a stream of hydrogen chloride gas there through.

GB934965 discloses improvements in the production of amino acid esters. Production of amino acid esters from lactams by using an esterifying alcohol in the presence of hydrogen chloride or hydrogen bromide and a substantial quantity of water followed by removal of water with a solvent capable of forming an azeotrope with water is described.

US20160068471 discloses ionic amino acid esters obtained by reacting unprotected alpha-amino acid with a fatty alcohol in the presence of an organic acid like carboxylate, mesylate, tosylate or sulfonate.

WO2015172158 discloses salts of ethanesulfonic acid alpha and higher amino acids esters.

JIN, S. Chemistry of Materials, 2011, Vol. 23, pages 2689 to 2692 and supporting information discloses salts of toluenesulfonic acid and alpha and higher amino acids esters.

There is a continuous need for an improved process for the preparation of amino acid esters and salts thereof which allows preparation of amino acid esters and salts thereof with high yield at fast reaction times, especially for esters of alcohols with boiling points significantly higher than 100° C., without handling of organic solvents and without handling of gaseous corrosive acids. There is also a need for a process which allows to react quantitatively amino acids and amino acid precursors such as lactams with alcohols with which have a low water solubility and can therefore only be dispersed in water to form amino acid esters and salts thereof.

There is a continuous need for amino acid esters salts with improved stability. Improved stability in aqueous alkaline solution of amino acid esters salts allows incorporation of amino acid esters salts in improved detergent formulations for fabric and home care applications such as hard surface cleaning.

It was an object of the present invention to provide a process which complies with the above identifies objectives and needs.

This goal was achieved by the present invention as described herein below and as reflected in the claims.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

Generally, as used herein, the term "obtainable by" means that corresponding products do not necessarily have to be produced (i.e. obtained) by the corresponding method or process described in the respective specific context, but also products are comprised which exhibit all features of a product produced (obtained) by said corresponding method or process, wherein said products were actually not produced (obtained) by such method or process. However, the term "obtainable by" also comprises the more limiting term "obtained by", i.e. products which were actually produced (obtained) by a method or process described in the respective specific context.

When used herein any definition requiring a compound or a substituent of a compound to consist of "at least a number of carbon atoms", number of carbon atoms refers to the total number of carbon atoms in said compound or substituent of a compound. For example for a substituent disclosed as "etheralkyl with at least 8 carbon atoms comprising alkylene oxide groups", the total number of at least 8 carbon atoms needs to be the sum of the number of carbon atoms of the alkyl moiety and the number of carbon atoms of the alkylene oxide moieties.

The present invention relates to a process for the synthesis of organic sulfonic acid salts of amino acid esters comprising the steps of
   (i) reacting at least one lactam with at least 3 carbon atoms in the lactam ring with at least one organic sulfonic acid in an aqueous solution,
   (ii) esterification of the reaction product of step (i) with at least one alcohol with at least 8 carbon atoms comprising at least one hydroxyl group, (iii) optionally removal of water and/or removal of excess alcohol of step (ii).

Lactams are cyclic amides, starting with α-lactam (three ring atoms) followed by β-lactam (four ring atoms), γ-lactam (five ring atoms) and so on. When hydrolyzed, lactams form the corresponding α-, β-, γ-amino acid. All lactams with at least three carbon atoms in the lactam ring can be used in the process for the synthesis of organic sulfonic acid salts. In one embodiment of the present invention, lactams with of from four to twelve carbon atoms in the lactam ring are used. In another embodiment of the present invention, lactams with of from five to seven carbon atoms in the lactam ring are used. In a further embodiment, a lactam with six carbon atoms in the lactam ring, ε-lactam, is used.

Reaction of the lactam ring takes place by reacting the at least one lactam with at least one organic sulfonic acid in the presence of water. In one embodiment of the present invention the reaction of the at least one lactam with at least one organic sulfonic acid in the presence of water is carried out as a separate step (i) of the process. In another embodiment the reaction of the at least one lactam with at least one organic sulfonic acid in the presence of water is carried out in combination with step (ii), the reaction with at least one alcohol with at least 8 carbon atoms comprising at least one hydroxyl group.

The at least one organic sulfonic acid is selected from the group consisting of alkylsulfonic acids, alkarylsulfonic acids, alkylenesulfonic acids, camphorsulfonic acid, and mixtures thereof. In one embodiment of the present invention the organic sulfonic acid is of the general formula R—S(=O)$_2$—OH where R is an alkyl group, alkaryl group, alkenyl group or aryl group. In another embodiment the organic sulfonic acid is of the general formula R—S(=O)$_2$—OH where R is an alkyl group or alkaryl group. In another embodiment of the invention the organic sulfonic acid is of the general formula R—S(=O)$_2$—OH where R is a branched or linear $C_1$- to $C_{36}$-alkyl group. In a further embodiment the organic sulfonic acid is of the general formula R—S(=O)$_2$—OH where R is a branched or linear $C_4$- to $C_{12}$-alkyl group. In another embodiment the organic sulfonic acid is methanesulfonic acid.

In a further embodiment the organic sulfonic acid is an alkylbenzene sulfonic acid. In another embodiment the organic sulfonic acid is a $C_4$- to $C_{20}$-alkyl benzene sulfonic acid. In a further embodiment the organic sulfonic acid is selected from the group consisting of 2, 6-dimethylbenzene sulfonic acid, 2, 5-dimethylbenzene sulfonic acid, 2, 4-dimethylbenzene sulfonic acid, and mixtures thereof. In a further embodiment the organic sulfonic acid is 4-dodecylbenzene sulfonic acid. In another embodiment the organic sulfonic acid is selected from the group consisting of isopropyl benzene sulfonic acid, ethylbenzenesulfonic acid, and naphthalene sulfonic acid. In another embodiment the organic sulfonic acid is selected from the group consisting of dodecylbenzene sulfonic acid, p-toluene sulfonic acid, xylene sulfonic acid, and methanesulfonic acid. In yet another embodiment the organic sulfonic acid is p-toluene sulfonic acid.

In one embodiment of the present invention, the lactam is selected from the group consisting of a lactam with five carbon atoms in the lactam ring, and a lactam with six carbon atoms in the lactam ring and the organic sulfonic acid is selected from the group consisting of methanesulfonic acid and alkylbenzene sulfonic acid. In another embodiment of the present invention, the lactam has five carbon atoms in the lactam ring and the organic sulfonic acid is methanesulfonic acid. In a further embodiment the lactam has five carbon atoms in the lactam ring and the organic sulfonic acid is alkylbenzene sulfonic acid. In another embodiment of the present invention, the lactam has six carbon atoms in the lactam ring and the organic sulfonic acid is methanesulfonic acid. In a further embodiment the lactam has six carbon atoms in the lactam ring and the organic sulfonic acid is alkylbenzene sulfonic acid.

In one embodiment the lactam is either dissolved in water or is dispersed in an aqueous phase. Typical concentration of lactam in water is in the range of from 50% by weight to 99% by weight based on the total weight of lactam and water. In one embodiment of the present invention the concentration of lactam in water is in the range of from 55 to 90% by weight based on the total weight of the lactam and water. In a further embodiment the concentration of lactam in water is in the range of from 65 to 80% by weight based on the total weight of the lactam and water. At least one organic sulfonic acid is either used as liquid at temperatures above its melting point or dissolved in water. Typical concentration of organic sulfonic acid dissolved in water is in the range of from 50% by weight to 95% by weight based on the total weight of solution.

In one embodiment of the present invention the concentration of organic sulfonic acid dissolved in water is in the range of from 60% by weight to 80% by weight based on the total weight of solution. In one embodiment of the present invention the total amount of organic sulfonic acid is added at the beginning of the reaction to the aqueous solution of the at least one lactam. In another embodiment, the at least one organic sulfonic acid is added dropwise for a duration of from 0.1 to 10 h to the at least one lactam which is already either an aqueous solution or dispersed in water.

The molar ratio of organic sulfonic acid to lactam is in the range of from 90 to 200 mol-%. In another embodiment of the present invention the molar ratio of organic sulfonic acid to lactam is in the range of from 100 to 150 mol-%. In another embodiment the molar ratio of organic sulfonic acid to lactam is in the range of from 100 to 125 mol-%. In a further embodiment the molar ratio of organic sulfonic acid to lactam is in the range of from 110 to 120 mol-%.

In all embodiments of the present invention no additional solvent other than water is present in step (i) of the process.

The reaction of the at least one lactam with at least one organic sulfonic acid is carried out at temperatures of from 50 to 150° C. In one embodiment of the invention, the reaction is carried out at temperatures of from 80 to 140° C. In another embodiment the reaction is carried out at temperatures of from 90 to 130° C. In one embodiment of the present invention, the temperature is kept constant for the duration of the reaction. In another embodiment, the temperature is varied within the temperature range during the duration of the reaction. The reaction of the at least one lactam with at least one organic sulfonic acid is carried out for a duration of from 0.1 to 10 hours. In another embodiment of the present invention the duration is of from 1 to 7 hours. In another embodiment the duration is of from 2 to 5 hours. In one embodiment of the present invention the reaction of the at least one lactam with at least one organic acid is carried out under atmospheric pressure. In one embodiment a protective atmosphere of for example nitrogen gas or argon gas is used to carry out the reaction. In another embodiment the reaction of the at least one lactam with at least one organic sulfonic acid is carried out at a temperature of from 50 to 150° C. at atmospheric pressure for a duration of 0.1 to 10 h. In a further embodiment of the present invention the reaction of the at least one lactam with at least one organic sulfonic acid is carried at a temperature of from 90 to 130° C. for 3 hours under atmospheric pressure.

Esterification takes place by reaction of the organic sulfonic amino acid salt formed by the reaction of step (i) with at least one alcohol with at least 8 carbon atoms comprising at least one hydroxyl group. In one embodiment of the present invention the esterification reaction of the organic sulfonic amino acid salt formed by the reaction of step (i) with at least one alcohol with at least 8 carbon atoms comprising at least one hydroxyl group takes place as a separate step (ii) of the process. In another embodiment the esterification reaction step (ii) takes place in parallel with step (i), the hydrolysis reaction of the process, thereby step (i) and step (ii) of the process are carried out in one single step.

If step (ii) takes place as a separate step following step (i) of the process, the reaction of step (i) is carried out until the hydrolysis of the lactam ring is completed. Completed is to be understood in the sense of that no more hydrolysis can take place, either because all lactam rings are hydrolyzed or because no more hydrolysis is possible given the chemical nature of the reaction partners and their amounts.

Following complete hydrolysis at least one alcohol with at least 8 carbon atoms comprising at least one hydroxyl group is added to the reaction mixture. The alcohol is added either without additional solvent or dissolved in water. In one embodiment of the present invention, the alcohol is selected from the group consisting of mono-alcohols, diols, polyols, alkoxylated mono-alcohols, alkoxylated diols, and alkoxylated polyols with at least 8 carbon atoms. In another embodiment of the present invention, at least one linear or branched $C_8$- to $C_{36}$-alcohol comprising at least one hydroxyl group is used. In one embodiment, alcohols are alkoxylated with ethylene oxide, and/or propylene oxide, and/or butylene oxide. Alkoxylation is either carried out with only one alkylene oxide or with more than one alkylene oxide. If more than one alkylene oxide is used, the resulting alkoxylates alcohols comprises either randomly distributed alkylene oxide units or a block of one alkylene oxide followed by a block of another alkylene oxide. In one embodiment of the present invention, alcohols alkoxylated with only a single alkylene oxide are used. In a further embodiment, alcohols alkoxylated with a first alkylene oxide followed by alkoxylation with a second alkylene oxide, thereby forming a block structure of different alkylene oxide blocks, are used. In even another embodiment, alkoxylated 2-propylheptanole was used.

In another embodiment, at least one alcohol selected from the group consisting of non-alkoxylated linear $C_8$- to $C_{36}$-alcohols, non-alkoxylated branched $C_8$- to $C_{36}$-alcohols, alkoxylated linear $C_8$- to $C_{36}$-alcohols, and alkoxylated branched $C_8$- to $C_{36}$-alcohols is used. In another embodiment the alcohol used in step (ii) is selected from the group consisting of a non-alkoxylated or alkoxylated, linear or branched $C_8$- to $C_{36}$-mono-alcohol. In another embodiment at least one $C_{12}$- to $C_{22}$-fatty alcohol is used. In another embodiment a mixture of $C_{16}$- and $C_{18}$-fatty alcohols is used. In another embodiment a mixture of $C_{18}$- and $C_{22}$-fatty alcohols is used. In a further embodiment linear or branched $C_8$- to $C_{10}$-mono-alcohols are used. In a further embodiment 2-propylheptanol or 2-ethylhexanol are used. In an even further embodiment 2-ethylhexanol is used.

In a further embodiment of the present invention, at least one phenoxyalkanol is used. In another embodiment phenoxyethanol is used.

The molar ratio of organic sulfonic amino acid salt of step (i) is in the range of from 50 to 125 mol-% in case a monoalcohol is used in step (ii). The molar ratio of organic sulfonic amino acid salt of step (i) to hydroxyl groups is in the range of from 10 to 125 mol-% in case a di- or polyalcohol is used in step (ii). In another embodiment of the present invention the molar ratio of organic sulfonic amino acid salt of step (i) to hydroxyl groups of the di- or polyalcohol of step (ii) is in the range of from 25 to 100 mol-%. In a further embodiment the molar ratio of organic sulfonic amino acid salt of step (i) to hydroxyl groups of the alcohol of step (ii) is in the range of from 100 to 125 mol-%.

The esterification reaction of step (ii) is carried out at temperatures in the range of from 80 to 200° C. In another embodiment of the present invention the esterification reaction is carried out at temperatures in the range of from 120 to 140° C. In one embodiment of the present invention, the temperature is kept constant for the duration of the reaction. In another embodiment, the temperature is varied within the temperature range during the duration of the reaction. The duration of the esterification reaction of step (ii) is from 1 to 30 h. In another embodiment of the present invention, the duration of the esterification reaction is from 2 to 5 h. In one embodiment vacuum in the range of from 0.1 mbar to 800 mbar is applied. In another embodiment vacuum in the range of from 1 mbar to 500 mbar is applied. In a further embodiment vacuum in the range of from 10 mbar to 100 mbar is applied.

Step (i) and step (ii) can be carried out in one single step. In this case at least one lactam, at least one organic sulfonic acid and at least one alcohol with at least 8 carbon atoms comprising at least one hydroxyl group are mixed to form an aqueous solution of an aqueous dispersion. The lactam is either dissolved in water or is dispersed in an aqueous phase. In one embodiment of the present invention concentrations of lactam in water are in the range of from 50% by weight to 99% by weight based on the total weight of lactam and water. In one embodiment of the present invention the concentration of lactam in water is in the range of from 55 to 90% by weight based on the total weight of the lactam and water. At least one organic sulfonic acid is either used as liquid at temperatures above its melting point or dissolved in water. Typical concentrations of organic sulfonic acid dissolved in water are in the range of from 50% by weight to 95% by weight based on the total weight of solution. In one embodiment of the present invention, the total amount of organic sulfonic acid is added at the beginning of the reaction to the aqueous solution of the at least one lactam and the at least one alcohol comprising at least one hydroxyl group. In another embodiment, the at least one organic sulfonic acid is added dropwise for a duration of from 0.1 to 10 h to the at least one lactam and at least one alcohol which are already either an aqueous solution or dispersed in water.

The combined reactions of step (i) and step (ii) are carried out at temperatures in the range of from 80 to 200° C. In another embodiment of the present invention the esterification reaction is carried out at temperatures in the range of from 120 to 140° C. In one embodiment of the present invention, the temperature is kept constant for the duration of the reaction. In another embodiment, the temperature is varied within the temperature range during the duration of the reaction. The duration of the esterification reaction of step (ii) is from 1 to 30 h. In another embodiment of the present invention, the duration of the esterification reaction is from 2 to 5 h. In one embodiment vacuum in the range of from 0.1 mbar to 800 mbar is applied. In another embodiment vacuum in the range of from 1 mbar to 500 mbar is applied. In a further embodiment vacuum in the range of from 10 mbar to 100 mbar is applied.

In all embodiments in which step (i) and step (ii) are carried out separately and in all embodiments in which step (i) and step (ii) are carried out in one single step no additional organic solvent other than the alcohol or mixture of alcohols used for the esterification of the organic sulfonic amino acid salt is present. Water is not an organic solvent.

In a further embodiment when step (i) and (ii) are carried out in one single step the process comprises reacting a mixture of at least one organic sulfonic acid, at least one lactam with at least 3 carbon atoms in the lactam ring and at least one linear or branched $C_8$- to $C_{36}$-alcohol comprising at least one hydroxyl group at a temperature of 80 to 200° C. for 1 to 10 h.

Following step (ii) or following the combined steps (i) and (ii) water and/or excess alcohol can be removed. Removal of water and alcohol can be carried out by all techniques known in the art, for example by application of a vacuum.

The invention also relates to organic sulfonic acid salt of an amino acid ester according to formula (I)

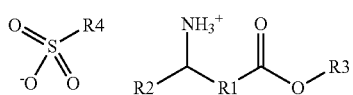

(I)

wherein R1 is a selected from the group consisting of methanediyl, ethanediyl, propanediyl, butanediyl, pentanediyl, hexanediyl, heptanediyl, octanediyl, nonanediyl, and decanediyl,
wherein R2 is H or $C_1$- to $C_{12}$-alkyl,
wherein R3 is a linear or branched, unmodified or modified with one or more hydroxy groups, alkyl with at least 8 carbon atoms, or a linear or branched, unmodified or modified with one or more hydroxy groups etheralkyl with at least 8 carbon atoms,
wherein R4 is selected from the group consisting of $C_3$-$C_{30}$-alkyl group, phenyl group, phenoxyalkyl group, alkaryl group except toluyl group, $C_3$-$C_{30}$-alkenyl group with at least one double bond in the alkene chain, camphor group, and mixtures thereof.

In one embodiment of the present invention, R1 is selected from the group consisting of propanediyl and butanediyl.

In one embodiment of the present invention, R2 is selected from the group consisting of hydrogen, methyl and ethyl. In a further embodiment, R2 is hydrogen.

In one embodiment of the present invention, R3 is a linear or branched $C_8$- to $C_{36}$-alkyl group. In another embodiment, R3 is a linear or branched $C_8$- to $C_{36}$-alkyl group with at least one hydroxyl group. In a further embodiment R3 is an etheralkyl with at least 8 carbon atoms comprising alkylene oxide groups terminated with a linear or branched alkyl group. In one embodiment R3 is an etheralkyl with at least 8 carbon atoms comprising ethylene oxide groups, and/or propylene oxide groups, and/or butylene oxide groups terminated with a linear or branched alkyl group. The alkoxyl groups are either selected from only one type of alkoxyl group or from more than one type of alkoxyl group. If more than one type of alkoxyl group is present, the resulting alkoxylates comprise either randomly distributed alkoxyl groups or a block of one type of alkoxyl groups followed by a block of another type of alkoxyl groups. In one embodiment of the present invention, etheralkyls with only one type of alkoxyl group are used. In a further embodiment, etheralkyls with a first type of alkoxyl groups followed by alkoxyl groups of a second type are used, which form a block structure of different alkoxyl groups.

In one embodiment R3 is a etheralkyl comprising a single alkylene oxide group terminated by a linear or branched $C_{10}$- to $C_{36}$-alkanol group. In even another embodiment R3 is an etheralkyl comprising an alkoxyl group block followed by a 2-propylheptyl group.

In another embodiment R3 is selected from the group consisting of $C_{12}$- to $C_{22}$-alkyl. In another embodiment R3 is selected from the group consisting of $C_{16}$- to $C_{18}$-alkyl. In another embodiment R3 is selected from the group consisting of $C_{18}$- and $C_{22}$-alkyl. In a further embodiment R3 is selected from linear or branched $C_8$- to $C_{10}$-alkyl. In a further embodiment R3 is 2-propylheptyl or 2-ethylhexyl. In an even further embodiment R3 is 2-ethylhexyl.

In one embodiment of the invention R4 is a branched or linear $C_4$- to $C_{20}$-alkyl group. In a further embodiment R4 is a branched or linear $C_4$- to $C_{12}$-alkyl group. In another embodiment R4 is (7,7-dimethyl-2-oxobicyclo[2.2.1]heptan-1-yl)methyl.

In one embodiment of the invention R4 is a linear or branched alkenyl group with at least one double bond in the alkenyl chain. In another embodiment R4 is a linear or branched $C_6$-$C_{30}$-alkenyl group with at least one double bond in the alkenyl chain. In a further embodiment the linear or branched alkenyl group of R4 is an beta or higher-olefinic $C_6$-$C_{30}$-alkenyl group.

In a further embodiment R4 is an alkyl benzyl group except a toluyl group. In another embodiment R4 is a $C_4$- to $C_{20}$-alkyl benzyl group. In a further embodiment R4 is selected from the group consisting of 2, 6-dimethylbenzyl, 2, 5-dimethylbenzyl, 2, 4-dimethylbenzyl, and mixtures thereof. In a further embodiment R4 is 4-dodecylbenzyl. In another embodiment R4 is selected from the group consisting of iso-propyl benzyl, ethyl benzyl, and naphthyl. In another embodiment R4 is a dodecylbenzyl group.

In a further embodiment R4 is a substituted phenyl group according to formula (II),

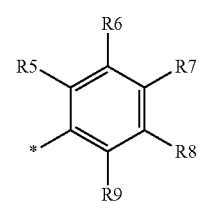

(II)

wherein the bond marked with * marks the bond connecting the group to the sulfur atom, and wherein R5, R6, R7, R8, and R9 are each independently selected from the group consisting of hydrogen, and linear and branched $C_1$- to $C_{20}$-alkyl groups, excluding the selection of one of R5 to R9 being methyl while the remaining groups are all hydrogen. In another embodiment R4 is a substituted phenyl group according to formula (II) wherein one of R5, R6, R7, R8, and R9 is a linear or branched $C_{11}$-alkyl group and the remaining substituent are hydrogen.

One embodiment of the present invention is directed to the organic sulfonic acid salt of an amino acid ester according to formula (I) wherein R1 is propanediyl and butanediyl, R2 is hydrogen, and R3 is linear or branched $C_8$- to $C_{36}$-alkyl. In a further embodiment R1 is propanediyl and butanediyl, R2 is hydrogen, R3 is linear or branched $C_8$- to $C_{36}$-alkyl, and R4 is an alkyl benzyl group excluding toluyl group. In another embodiment, R1 is butanediyl, R2 is hydrogen, R3 is 2-propylheptyl or 2-ethylhexyl, and R4 is an alkyl benzyl group excluding toluyl. In a further embodiment, R1 is butanediyl, R2 is hydrogen, R3 is 2-propylheptyl, and R4 is dodecylbenzyl. In a further embodiment, R1 is butanediyl, R2 is hydrogen, R3 is 2-propylheptyl, and R4 xylyl. In a further embodiment, R1 is butanediyl, R2 is hydrogen, R3 is 2-ethylhexyl, and R4 is dodecylbenzyl. In another embodiment, R1 is butanediyl, R2 is hydrogen, R3 is 2-ethylhexyl, and R4 is xylyl. In one embodiment of the present invention the organic sulfonic acid salt of an amino acid ester according to formula (I) R1 is butanediyl, R2 is H, R3 is phenoxyethyl and R4 is dodecylbenzyl.

EXAMPLES

Methods
$^1$H NMR measured in MeOD with Bruker Avance 400 MHz spectrometer.

Example 1

In a 4-neck vessel with thermometer, reflux condenser, nitrogen inlet, dropping funnel, and stirrer, 141.45 g caprolactam (80 wt.-% aqueous solution) are placed and heated to 70° C. At this temperature 140.04 g methane sulfonic acid (70 wt.-% aqueous solution) are added within 20 minutes. Temperature is raised to 118° C. and the mixture is stirred for 3 hours. The mixture is cooled to 90° C. and 156.27 g 2-ethylhexanol are added within 20 minutes. The reaction mixture is heated to 120° C. and vacuum (950-850 mbar) is applied to remove the water. After 3 hours at 120° C. the vacuum is lowered to 20 mbar. The reaction mixture is stirred for 2.5 hours at 20 mbar and 130° C. 332.0 g of a light brown solid is obtained. $^1$H-NMR in MeOD indicates complete conversion to 6-amino-hexane acid-2-ethylhexylester methane sulfonic acid salt.

Example 2

In a 4-neck vessel with thermometer, reflux condenser, nitrogen inlet, dropping funnel, and stirrer, 141.45 g caprolactam (80 wt.-% aqueous solution) and 156.27 g 2-ethylhexanol are placed and heated to 40° C. At this temperature 140.04 g methane sulfonic acid (70 wt.-% aqueous solution) are added within 20 minutes. Temperature is raised to 110° C. and the mixture is stirred for 3 hours at 110° C. Vacuum is applied and lowered to 20 mbar, simultaneously the temperature is raised to 140° C. The reaction mixture is stirred for 2.5 hours at 20 mbar and 140° C. 330.0 g of a light brown solid is obtained. $^1$H-NMR in MeOD indicates complete conversion to 6-amino-hexane acid-2-ethylhexylester methane sulfonic acid salt.

Example 3

In a 4-neck vessel with thermometer, reflux condenser, nitrogen inlet, dropping funnel, and stirrer, 19.3 g caprolactam (80 wt.-% aqueous solution) and 38.7 g Cis/Cis fatty alcohol (hydroxyl value 217.4 mgKOH/g) are placed and heated to 70° C. At this temperature 27.3 g methane sulfonic acid (70 wt.-% aqueous solution) are added within 20 minutes. Temperature is raised to 120° C. and the homogeneous mixture is stirred for 3 hours at 120° C. Vacuum is applied and lowered to 20 mbar, simultaneously the temperature is raised to 138° C. The reaction mixture is stirred for 8 hours at 20 mbar and 140° C. 65.5 g of a light brown solid is obtained. $^1$H-NMR in MeOD indicates complete conversion to 6-amino-hexane acid-Cis/Cis fatty alcohol ester methane sulfonic acid salt.

Example 4

In a 4-neck vessel with thermometer, reflux condenser, nitrogen inlet, dropping funnel, and stirrer, 19.3 g caprolactam (80 wt.-% aqueous solution) and 44.6 g Cis/$C_{22}$ fatty alcohol (hydroxyl value 188.6 mgKOH/g) are placed and heated to 70° C. At this temperature 27.3 g methane sulfonic acid (70 wt.-% aqueous solution) are added within 20 minutes. Temperature is raised to 120° C. and the homogeneous mixture is stirred for 3 hours at 126° C. Vacuum is applied and lowered to 20 mbar, simultaneously the temperature is raised to 138° C. The reaction mixture is stirred for 8 hours at 20 mbar and 140° C. 71.4 g of a light brown solid is obtained. $^1$H-NMR in MeOD indicates complete conversion to 6-amino-hexane acid-$C_{18}$/$C_{22}$ fatty alcohol ester methane sulfonic acid salt.

Example 5

In a 4-neck vessel with thermometer, reflux condenser, nitrogen inlet, dropping funnel, and stirrer, 21.3 g 2-pyrrolidon and 39.1 g 2-ethylhexanol are placed and heated to 50° C. At this temperature 35.0 g methane sulfonic acid (70 wt.-% aqueous solution) are added within 20 minutes. Temperature is raised to 104° C. and the mixture is stirred for 3 hours at 104° C.-110° C. Vacuum is applied and lowered to 20 mbar, simultaneously the temperature is raised to 135° C. The reaction mixture is stirred for 2.5 hours at 20 mbar and 135° C. 75.0 g of a light brown solid is obtained. $^1$H-NMR in MeOD indicates complete conversion to 4-amino-butane acid-2-ethylhexylester methane sulfonic acid salt.

Example 6

In a 4-neck vessel with thermometer, reflux condenser, nitrogen inlet, dropping funnel, and stirrer, 24.7 g 2-piperidon and 39.6 g 2-ethylhexanol are placed and heated to 50° C. At this temperature 35.0 g methane sulfonic acid (70 wt.-% aqueous solution) are added within 20 minutes. Temperature is raised to 104° C. and the mixture is stirred for 5.5 hours at 104° C.-110° C. Vacuum is applied and lowered to 20 mbar, simultaneously the temperature is raised to 135° C. The reaction mixture is stirred for 2.5 hours at 20 mbar and 135° C. 81.0 g of a light brown solid is obtained. $^1$H-NMR in MeOD indicates complete conversion to 4-amino-pentane acid-2-ethylhexylester methane sulfonic acid salt.

Example 7

In a 4-neck vessel with thermometer, reflux condenser, nitrogen inlet, dropping funnel, and stirrer, 35.4 g caprolactam (80 wt.-% aqueous solution) and 35.8 g 2-ethylhexanol are placed and heated to 45° C. At this temperature 48.5 g p-toluene sulfonic acid are added in portions within 20 minutes. Temperature is raised to 110° C. and the mixture is stirred for 4 hours at 110° C. Vacuum is applied and lowered to 20 mbar, simultaneously the temperature is raised to 140° C. The reaction mixture is stirred for 5 hours at 20 mbar and 140° C. 95.0 g of a light brown solid is obtained. $^1$H-NMR in MeOD indicates 88% conversion to 6-amino-hexane acid-2-ethylhexylester p-toluene sulfonic acid salt.

Example 8

In a 4-neck vessel with thermometer, reflux condenser, nitrogen inlet, dropping funnel, and stirrer, 21.3 g caprolactam (80 wt.-% aqueous solution) and 43.6 g 2-Propylheptanol, ethoxylated with 3 mole ethyleneoxide are placed and heated to 45° C. At this temperature 52.6 g 4-dodecyl benzene sulfonic acid (mixture of isomers) are added within 20 minutes. Temperature is raised to 133° C. and the mixture is stirred for 4 hours at 133° C. Vacuum is applied and lowered to 5 mbar, simultaneously the temperature is raised to 140° C. The reaction mixture is stirred for 5 hours at 5 mbar and 140° C. 99.0 g of a brown oil is obtained. $^1$H-NMR in MeOD indicates 82% conversion to 6-amino hexane acid acid-triethylene glycol 2-propyl-heptylether ester as 4-dodecylbenzene sulfonic acid (mixture of isomers) salt.

Example 9

In a 4-neck vessel with thermometer, reflux condenser, nitrogen inlet, dropping funnel, and stirrer, 21.2 g caprolactam (80% aqueous solution) and 26.1 g 2-propylheptanol are placed and heated to 40° C. At this temperature 52.6 g 4-dodecyl benzene sulfonic acid (mixture of isomers) are added within 20 minutes. Temperature is raised to 110° C. and the mixture is stirred for 4 hours at 110° C. The mixture is heated to 130° C. and formed water is distilled off for 5 hours. Vacuum is applied and lowered to 4 mbar, simultaneously the temperature is raised to 140° C. The reaction mixture is stirred for 4 hours at 4 mbar and 140° C. 77.0 g of a brown oil is obtained. 1H-NMR in MeOD indicates 81% conversion to 6-amino-hexane acid-2-propylheptylester 4-dodecyl benzene sulfonic acid (mixture of isomers) salt.

Example 10

In a 4-neck vessel with thermometer, reflux condenser, nitrogen inlet, dropping funnel, and stirrer, 21.2 g caprolactam (80 wt.-% aqueous solution) and 5.0 g water are placed and heated to 70° C. At this temperature 52.6 g 4-dodecyl benzene sulfonic acid (mixture of isomers) are added within 20 minutes. Temperature is raised to 118° C. and the mixture is stirred for 4 hours. The mixture is cooled to 90° C. and 21.5 g 2-ethylhexanol are added within 20 minutes. The reaction mixture is heated to 120° C. and vacuum (950-850 mbar) is applied to remove the water. After 3 hours at 120° C. the vacuum is lowered to 20 mbar. The reaction mixture is stirred for 2.5 hours at 20 mbar and 130° C. 77.4 g of a light brown oil is obtained. $^1$H-NMR in MeOD indicates 73% conversion to 6-amino-hexane acid-2-ethylhexylester 4-dodecyl benzene sulfonic acid (mixture of isomers) salt.

Example 11

In a 4-neck vessel with thermometer, reflux condenser, nitrogen inlet, dropping funnel, and stirrer, 21.5 g 2-ethylhexanol and 19.7 g 6-amino hexane acid are placed and heated to 50° C. To the mixture 52.6 g 4-dodecyl benzene sulfonic acid (mixture of isomers) is added within 10 minutes. The reaction mixture is heated to 133° C. and is stirred for 4 hours at 133° C., formed water is distilled off. Excess 2-ethylhexanol and volatile compounds are removed in vacuo (7 mbar) at elevated temperature (140° C.) and 80.7 g of a light brown oil is obtained. $^1$H-NMR in MeOD indicates complete conversion to 6-amino-hexane acid-2-ethylhexylester 4-dodecylbenzene sulfonic acid salt.

Example 12

In a 4-neck vessel with thermometer, reflux condenser, nitrogen inlet, dropping funnel, and stirrer, 43.6 g 2-Propylheptanol, ethoxylated with 3 mole ethylenoxide and 19.7 g 6-amino hexane acid are placed and heated to 90° C. To the mixture 52.6 g 4-dodecyl benzene sulfonic acid (mixture of isomers) is added within 10 minutes. The reaction mixture is heated to 135° C. and is stirred for 4 hours at 135° C. Vacuum (5 mbar) is applied and the reaction mixture is stirred for additional 10 hours at 140° C. 102.1 g of a light brown solid is obtained. $^1$H-NMR in MeOD indicates complete conversion to 6-amino hexane acid acid-triethylene glycol 2-propyl-heptylether ester as 4-dodecylbenzene sulfonic acid (mixture of isomers) salt.

Example 13

In a 4-neck vessel with thermometer, reflux condenser, nitrogen inlet, dropping funnel, and stirrer, 42.4 g caprolactam (80% aqueous solution), 41.4 g phenoxyethanol and 18.5 g water are placed and heated to 40° C. At this temperature 99.9 g 4-dodecyl benzene sulfonic acid (mixture of isomers) are added within 10 minutes. The mixture is heated to reflux (approx. 100° C.) and stirred for 4 h under reflux. Vacuum is applied and lowered to 350 mbar, simultaneously the temperature is raised to 130° C. The reaction mixture is stirred for 5 hours at 350 mbar and 130° C. To remove residual water, the vacuum is lowered to 10 mbar, and the mixture is stirred for 2 h at 130° C. and 10 mbar. 160.0 g of a brown oil is obtained. $^1$H-NMR in MeOD indicates 99.5% conversion to 6-amino hexane acid acid-phenoxyethanol-ester as 4-dodecylbenzene sulfonic acid (mixture of isomers) salt.

Example 14

In a 4-neck vessel with thermometer, reflux condenser, nitrogen inlet, dropping funnel, and stirrer, 62.2 g caprolactam (80% aqueous solution), and 67.5 g phenoxyethanol are placed and heated to 40° C. At this temperature 61.6 g methane sulfonic acid (70% aqueous solution) are added within 10 minutes. The mixture is heated to reflux (approx. 100° C.) and stirred for 4 h under reflux. Vacuum is applied and lowered stepwise to 10 mbar, simultaneously the temperature is raised to 130° C. The reaction mixture is stirred for 10 hours at 10 mbar and 130° C. 149.0 g of a brown solid is obtained. $^1$H-NMR in MeOD indicates 97.2% conversion to 6-amino hexane acid acid-phenoxyethanol-ester as methane sulfonic acid salt.

Comparative Example 1

In a 4-neck vessel with thermometer, reflux condenser, nitrogen inlet, dropping funnel, and stirrer, 56.58 g caprolactam (80% in water) and 44.47 g i-butanol are placed and heated to 46° C. At this temperature 56.01 g methane sulfonic acid are added within 20 minutes. Temperature is allowed raised to 63° C. After complete addition of methane sulfonic acid, the temperature is raised to 104° C. (reflux), and the mixture is stirred for 11 hours at 105° C. Vacuum is applied and lowered to 20 mbar, to remove excess of i-butanol, and stirred for 1 hour. $^1$H-NMR in MeOD indicates a 45:55 mixture of 6-amino-hexane acid-i-butanolester methane sulfonic acid salt and non-esterified 6-amino-hexane acid methane sulfonic acid salt.

Stability in Alkaline Solution

To determine the stability under alkaline conditions, 50 wt % of the organic sulfonic acid salt of an amino acid ester is dissolved in water, pH is adjusted with sodium hydroxide to pH 8.5. The aqueous solution or emulsion is stored for 7 days at room temperature and 40° C. Before storage the integral of CH2-O—CO— ($^1$H-NMR in MeOD, ~4.2 ppm) is measured. The stability of organic sulfonic acid salt of an amino acid ester is indicated by measuring the integral of CH2-O—CO— ($^1$H-NMR in MeOD) after storage. The residual amount of ester bonds is calculated:

$$\text{Residual amount ester bond } [\%] = \frac{\text{integral CH2—O—CO— after storage}}{\text{integral CH2—O—CO— before storage}} \times 100$$

TABLE 1

Residual amount of ester bonds after storage [%], calculated from $^1$H-NMR in MeOD

| | Reaction product of | 7 d pH 8.5 RT | 7 d pH 8.5 40° C. |
|---|---|---|---|
| Comparative example 2 | 2-Ethylhexanol and Lysine, methane sulfonic acid salt | 59 | 15 |
| Comparative example 3 | 2-Ethylhexanol + Glycine, methane sulfonic acid salt | 37 | 20 |
| Comparative example 4 | 2-Ethylhexanol + Alanine, methane sulfonic acid salt | 72 | 46 |
| Comparative example 5 | 2-Ethylhexanol + Alanine, dodecylbenzene sulfonic acid salt | 63 | 60 |
| Example 11 | 2-Ethylhexanol + 6-Aminohexane acid, dodecylbenzene sulfonic acid salt | 100 | 100 |

*Comparative examples 2 to 5 were prepared analog to the procedure disclosed in Example 11.

Use as Additives in Detergents

Technical stain swatches of blue knitted cotton containing Bacon Grease were purchased from Warwick Equest Ltd. The stains were washed for 30 min in a launder-o-meter (manufactured by SDL Atlas) at room temperature using per canister 500 mL of washing solution, 20 metal balls and ballast fabrics. The washing solution contained 5000 ppm of detergent composition DC1 (table 2). Water hardness was 2.5 mM ($Ca^{2+}$:$Mg^{2+}$ was 4:1). Additives were added to the washing solution of each canister separately and in the amount as detailed below. After addition the pH value was re-adjusted to the pH value of washing solution without additive. Standard colorimetric measurement was used to obtain L*, a* and b* values for each stain before and after the washing. From L*, a* and b* values the stain level were calculated as color difference ΔE (calculated according to DIN EN ISO 11664-4) between stain and untreated fabric.

Stain removal from the swatches was calculated as follows:

$$\text{Stain Removal Index } (SRI) = \frac{\Delta E_{initial} - \Delta E_{washed}}{\Delta E_{initial}} \times 100$$

$\Delta E_{initial}$=Stain level before washing
$\Delta E_{washed}$=Stain level after washing Stain level corresponds to the amount of grease on the fabric. The stain level of the fabric before the washing ($\Delta E_{initial}$) is high, in the washing process stains are removed and the stain level after washing is smaller ($\Delta E_{washed}$). The better the stains have been removed the lower the value for $\Delta E_{washed}$ will be and the higher the difference will be to $\Delta E_{initial}$. Therefore, the value of stain removal index increases with better washing performance.

TABLE 2

Detergent composition DC1

| Ingredients of liquid detergent composition DC1 | percentage by weight |
|---|---|
| n-$C_{10}$-$C_{13}$-alkylbenzene sulfonic acid | 5.3 |
| coconut $C_{12}$-$C_{18}$ fatty acid | 2.4 |
| sodium laureth sulfate + 2 EO | 7.7 |
| potassium hydroxide | 2.2 |
| $C_{13}C_{15}$- oxo alcohol + 7 EO | 5.4 |
| 1,2 propylene glycol | 6 |
| ethanol | 2 |
| water pH of detergent composition DC1 = 8.0 | To Balance |

TABLE 3

Washing Experiment

| | SRI, Bacon Graese Cleaning |
|---|---|
| Without additive | 10.6 |
| Product of example 7 (2-Ethylhexanol, ester with 6-amino hexane acid, toluenesulfonic acid salt); 0.15 g per wash | 38.4 |
| Product of example 8 (2-Propylheptanol, ethoxylated with 3 mole ethylenoxide, ester with 6-amino hexane acid, 4-dodecylbenzene sulfonic acid (mixture of isomers) salt); 0.1825 g per wash | 31.5 |
| Product of example 8 (2-Propylheptanol, ethoxylated with 3 mole ethylenoxide, ester with 6-amino hexane acid, 4-dodecylbenzene sulfonic acid (mixture of isomers) salt); 0.2012 g per wash | 31.8 |
| Product of example 10 (2-ethyl-hexanol, ester with 6-amino hexane acid, 4-dodecylbenzene sulfonic acid (mixture of isomers) salt); 0.2546 g per wash | 50.4 |

The invention claimed is:

1. Process for the synthesis of organic sulfonic acid salts of amino acid esters comprising the steps of
   (i) reacting at least one lactam with at least 3 carbon atoms in the lactam ring with at least one organic sulfonic acid in an aqueous solution,
   (ii) esterification of the reaction product of step (i) with at least one alcohol with at least 8 carbon atoms comprising at least one hydroxyl group,
   (iii) optionally removal of water and/or removal of excess alcohol of step (ii);
   wherein the aqueous solution has a molar ratio of water to the at least one lactam of at least 2.33:1.

2. Process according to claim 1, wherein step (i) and (ii) are carried out in one single step.

3. Process according to claim 1, wherein the molar ratio of organic sulfonic acid to lactam is in the range of from 90 to 200 mol-%.

4. Process according to claim 2, wherein the combined step (i) and (ii) comprises reacting a mixture of organic sulfonic acid, at least one lactam with at least 3 carbon atoms in the lactam ring and at least one linear or branched $C_8$- to $C_{36}$-alcohol comprising at least one hydroxyl group at a temperature of 80 to 200° C. for 1 to 30 h.

5. Process according to claim 1, wherein the molar ratio of organic sulfonic amino acid salt reaction product of step (i) to hydroxyl groups of the at least one alcohol is in the range of from 50 to 125 mol-% in case a monoalcohol is used in step (ii).

6. Process according to claim 1, wherein the molar ratio of organic sulfonic amino acid salt reaction product of step (i) to hydroxyl groups of the at least one alcohol is in the range of from 10 to 125 mol-% in case a di- or polyalcohol is used in step (ii).

7. Process according to claim 1, wherein the alcohol used in step (ii) is selected from the group consisting of mono-alcohols, diols, polyols, alkoxylated mono-alcohols, alkoxylated diols, and alkoxylated polyols.

8. Process according to claim 1, wherein the lactam used in step (i) is a ε-lactam.

9. Process according to claim 1, wherein the organic sulfonic acid is selected from the group consisting of dodecylbenzene sulfonic acid, p-toluene sulfonic acid, xylene sulfonic acid, and methanesulfonic acid.

10. Process according to claim 1, wherein the organic sulfonic acid is methanesulfonic acid.

11. Process for the synthesis of organic sulfonic acid salts of amino acid esters comprising the steps of
(i) reacting at least one lactam with at least 3 carbon atoms in the lactam ring with at least one organic sulfonic acid in an aqueous solution,
(ii) esterification of the reaction product of step (i) with at least one alcohol with at least 8 carbon atoms comprising at least one hydroxyl group,
(iii) optionally removal of water and/or removal of excess alcohol of step (ii);
wherein the at least one organic sulfonic acid is not p-toluene sulfonic acid; and wherein the aqueous solution has a molar ratio of water to the at least one lactam of at least 2.33:1.

12. The process according to claim 1, wherein the aqueous solution has a molar ratio of water to the at least one lactam of 2.33:1 to 5:1.

* * * * *